United States Patent [19]

Nishizono

[11] 4,443,469

[45] Apr. 17, 1984

[54] URIC ACID-LOWERING COMPOSITION, METHOD AND USE

[75] Inventor: Masahisa Nishizono, Fukuoka, Japan

[73] Assignee: Fujisawa Pharmaceutical Co., Ltd., Osaka, Japan

[21] Appl. No.: 421,096

[22] Filed: Sep. 22, 1982

[30] Foreign Application Priority Data

Sep. 24, 1981 [JP] Japan .................................. 56-151062

[51] Int. Cl.³ ............................................. A61K 31/38
[52] U.S. Cl. .................................................... 424/275
[58] Field of Search ........................................ 424/275

[56] References Cited

FOREIGN PATENT DOCUMENTS 1247067 9/1971 United Kingdom .

*Primary Examiner*—Stanley J. Friedman
*Attorney, Agent, or Firm*—Oblon, Fisher, Spivak, McClelland & Maier

[57] ABSTRACT

The lowering of uric-acid levels with 2-chloro-11-(2-dimethylaminoethoxy)dibenzo[b,f]thiepin.

3 Claims, No Drawings

URIC ACID-LOWERING COMPOSITION, METHOD AND USE

This invention relates to the discovery that 2-chloro-11-(2-dimethylaminoethoxy)dibenzo[b,f]thiepin (hereinafter referred to as "zotepine") or a pharmaceutically acceptable salt thereof possesses a uric acid-lowering property in the human body.

This invention relates, more particularly, to use of zotepine or its pharmaceutically acceptable salt as a uric acid-lowering agent for prophylaxis and therapy to human being, to method for preventing or treating gout by administering zotepine or its pharmaceutically acceptable salt or in a pharmaceutical form thereof to human being, and also to pharmaceutical composition of zotepine or its pharmaceutically acceptable salt useful as a uric acid-lowering agent.

Zotepine is a known compound having the following structural formula:

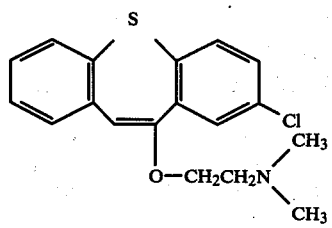

Zotepine and its pharmaceutically acceptable salt are known to have psychotropic activity but have never been known to have an activity to lower the level of uric acid in human body.

The present inventors found that zotepine and its pharmaceutically acceptable salt have such an activity to lower the uric acid level in the human body and are of value as a uric acid-lowering agent. This invention is predicated on the above finding.

The uric acid-lowering agent according to this invention can be used in various pharmaceutical compositions for the treatment and prophylaxis of gout, and can be administered via oral or parenteral route.

The above-mentioned pharmaceutical compositions can be used in a conventional pharmaceutical forms such as capsules, microcapules, granules, powders, tablets, syrups, etc.

Moreover, such pharmaceutical compositions are produced by the established pharmaceutical procedure using the conventional additives such as excipient (e.g. sucrose, starch, mannit, sorbit, lactose, glucose, cellulose, talc, calcium phosphate, calcium carbonate, etc.), binding agent (e.g. cellulose, methylcellulose, ethyl cellulose, hydroxypropylcellulose, polypropylpyrrolidone, gelatine, gum arbic, polyethyleneglycol, sucrose, starch, etc.), disintegrator (e.g. starch, carboxymethylcellulose, calcium salt of carboxymethyl cellulose, hydroxypropylstarch, sodium glycole-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), etc.

While the dosage of the uric acid-lowering agent according to this invention depends on the patient's age, body weight, condition, etc., it is generally administered by the oral route at the daily dose level of 3 to 450 mg as zotepine or said salt thereof, preferably 5 to 100 mg on the same basis, at the interval of 1 to 3 times a day. Typical unit doses may be 1 mg, 5 mg, 10 mg, 15 mg, 20 mg and 25 mg, although these are only examples and not limitative, of course.

The uric acid-lowering action of zotepine in the human body is explained in the following.

EXPERIMENTAL TEST 1

Subjects

A total of 12 cases, consisting of 6 schizophrenic patients with enhanced irritability and excitement, 4 patients in manic state, and 2 neurotic patients with enhanced irritability and aggression.

Dosage 25 mg/day: 7 cases
50 mg/day: 3 cases
75 mg/day: 2 cases

The above dosage was administered in 3 divided doses daily for a week.

Method for assay of serum uric acid

Blood samples were taken from the patients before breakfast and the uric acid level in each serum sample was determined by the reduction (tungsten) method.

Results

See the table below.

|  |  | Serum uric acid (mg/dl) | |
| --- | --- | --- | --- |
| Dosage | Subject | Before administration of zotepine | 1 Week after administration |
| 25 mg/day | A | 8.0 | 2.7 |
|  | B | 6.1 | 3.5 |
|  | C | 4.8 | 3.2 |
|  | D | 6.2 | 3.7 |
|  | E | 6.4 | 4.5 |
|  | F | 5.2 | 3.3 |
|  | G | 5.4 | 3.6 |
| 50 mg/day | H | 5.8 | 2.3 |
|  | I | 4.9 | 3.2 |
|  | J | 4.8 | 3.3 |
| 75 mg/day | K | 2.8 | 1.7 |
|  | L | 8.9 | 4.3 |

Note:
Other psychotropic drugs which had been administered before zotepine therapy and were considered necessary for the treatment of mental diseases even after institution of zotepine therapy were continued without withdrawal.

EXPERIMENTAL TEST 2

6 mg and 15 mg of zotepine were respectively administered orally to a healthy adult man (22 years old) in 3 divided doses a day at a week interval.

Results

See the table below.

|  | Uric acid clearance (ml/min) | |
| --- | --- | --- |
| Dosage | before dosage | after dosage |
| 6 mg | 6 | 8 |
| 15 mg | 7 | 10 |

The acute toxicity of zotepine is as follows.

| Mouse (JCL: ICR strain) | |
| --- | --- |
| Oral, male | 108 mg/kg |
| female | 140 mg/kg |
| Rat (JCL: SD strain) | |
| Oral, male | 458 mg/kg |
| female | 306 mg/kg |
| Rabbit (New Zealand White strain) | |
| Oral, male | 458 mg/kg |
| female | 250 mg/kg |
| Dog (Mongrel) | |
| Oral, female | >1,000 mg/kg |

The following working examples are illustrative of this invention.

EXAMPLE 1

(Granules)

| Zotepine | 50 (g) |
| --- | --- |
| sucrose | 9700 |
| Hydroxypropylcellulose | 200 |
| Starch | 50 |

The above components are admixed and processed into granules by the established pharmaceutical procedure.

EXAMPLE 2

(Capsules)

| Zotepine | 50 (g) |
| --- | --- |
| Starch | 1987 |
| Magnesium stearate | 13 |

The above components are admixed and filled into the conventional hard gelatin capsules at the rate of 5 mg/capsule to provide 10,000 capsules.

EXAMPLE 3

(Tablets)

| Zotepine | 500 (g) |
| --- | --- |
| Lactose | 20800 |
| Starch | 7200 |
| Ethylcellulose | 3600 |
| Magnesium stearate | 400 |

The above components are admixed and tableted in the routine manner to provide 100,000 tablets each containing 5 mg of zotepine. These tablets are then sugar- or film-coated as necessary in the conventional manner to give sugar-coated or film-coated tablets.

EXAMPLE 4

(Tablets)

| Zotepine | 500 (g) |
| --- | --- |
| Lactose | 4200 |
| Starch | 1100 |
| Ethylcellulose | 600 |
| Magnesium stearate | 100 |

The above components are admixed and tableted in the routine manner to provide 100,000 tablets each containing 5 mg of zotepine. These tablets are then sugar- or film-coated as necessary in the conventional manner to give either sugar-coated or film-coated tablets.

What we claim is:

1. A method for treating gout which comprises administering a uric acid-lowering amount of 2-chloro-11-(2-dimethylaminoethyl) dibenzo [b,f]-thiepin or its pharmaceutically acceptable salt to a human being having uric acid abnormality.

2. The method of claim 1, wherein said compound is administered in the form of a shaped medicament.

3. The method of claim 1, wherein said compound with a pharmaceutically acceptable excipient is administered in the form of capsules, microcapsules, granules, powders, tablets or syrups.

* * * * *